US012800488B2

(12) United States Patent
Hasener et al.

(10) Patent No.: US 12,800,488 B2
(45) Date of Patent: Nov. 17, 2026

(54) METHOD FOR MONITORING THE MANUFACTURE OF WOOD-BASED PRODUCTS WITH REGARD TO THE EMISSION OF VOLATILE ORGANIC COMPOUNDS, AND DEVICES FOR MONITORING THE EMISSION OF VOLATILE ORGANIC COMPOUNDS IN THE MANUFACTURE OF WOOD-BASED PRODUCTS

(71) Applicant: Fagus-GreCon Greten GmbH & Co. KG, Alfeld (DE)

(72) Inventors: Joerg Hasener, Alfeld (DE); Manuel Fleisch, Langenhagen (DE); Markus Funke, Alfeld (DE)

(73) Assignee: Fagus-GreCon Greten GmbH & Co. KG, Alfeld (DE)

( * ) Notice: Subject to any disclaimer, the term of this patent is extended or adjusted under 35 U.S.C. 154(b) by 296 days.

(21) Appl. No.: 18/611,278

(22) Filed: Mar. 20, 2024

(65) Prior Publication Data

US 2024/0319089 A1 Sep. 26, 2024

(30) Foreign Application Priority Data

Mar. 22, 2023 (DE) ......................... 102023107151.3

(51) Int. Cl.
*G01N 21/39* (2006.01)
*G01N 33/00* (2006.01)
(Continued)

(52) U.S. Cl.
CPC ......... *G01N 21/39* (2013.01); *G01N 33/0047* (2013.01); *G01N 33/46* (2013.01); *B27M 3/00* (2013.01)

(58) Field of Classification Search
None
See application file for complete search history.

(56) References Cited

U.S. PATENT DOCUMENTS

2004/0094851 A1* 5/2004 Mbachu ................. B27N 1/029 264/109
2005/0241743 A1* 11/2005 Mbachu ............... G01N 21/274 73/1.01

(Continued)

FOREIGN PATENT DOCUMENTS

DE 69937675 T2 11/2008
DE 102007061666 B4 6/2009

(Continued)

OTHER PUBLICATIONS

English translation of EP2511703A1 (Year: 2026).*
English translation of DE102019114035A1 (Year: 2026).*

*Primary Examiner* — Mark A Shabman
(74) *Attorney, Agent, or Firm* — MUNCY, GEISSLER, OLDS & LOWE, P.C.

(57) ABSTRACT

A method for monitoring a manufacture of wood-based products includes at least one pressing process with regard to the emission of volatile organic compounds from the wood-based products, in which the concentration of the volatile organic compounds is detected during the manufacture. The concentration of the volatile organic compounds is detected during an extraction of product parts or of a product surface using a measurement method from the field of TDLS (Tunable Diode Laser Spectroscopy), FTIR, NIR, IMS or photoacoustics, that the detected concentration of the volatile organic compounds is fed to a mathematical model, and that parameters such as product thickness, areal density, production feed rate, flow rate in an extraction of product parts or of the product surface and the moisture content of the raw materials for the wood-based products are deter- (Continued)

mined before the pressing process and are also fed to the mathematical model.

19 Claims, 2 Drawing Sheets

(51) Int. Cl.
*G01N 33/46* (2006.01)
*B27M 3/00* (2006.01)

(56) References Cited

U.S. PATENT DOCUMENTS

| | | | | |
|---|---|---|---|---|
| 2007/0131862 | A1* | 6/2007 | Cowan | G01N 21/274<br>250/339.09 |
| 2009/0230306 | A1* | 9/2009 | Andre | G01N 21/359<br>250/339.09 |
| 2020/0284720 | A1* | 9/2020 | Wertli | G01J 3/0205 |
| 2022/0161541 | A1* | 5/2022 | Bolton | B32B 39/00 |

FOREIGN PATENT DOCUMENTS

| | | | | | |
|---|---|---|---|---|---|
| DE | 102011017280 | A1 | | 10/2012 | |
| DE | 202019102959 | U1 | | 10/2020 | |
| DE | 102019114035 | A1 | * | 11/2020 | G01N 27/622 |
| EP | 2511703 | A1 | * | 10/2012 | G01N 27/622 |
| WO | WO-2013/109853 | A1 | | 7/2013 | |

* cited by examiner

METHOD FOR MONITORING THE MANUFACTURE OF WOOD-BASED PRODUCTS WITH REGARD TO THE EMISSION OF VOLATILE ORGANIC COMPOUNDS, AND DEVICES FOR MONITORING THE EMISSION OF VOLATILE ORGANIC COMPOUNDS IN THE MANUFACTURE OF WOOD-BASED PRODUCTS

Method for monitoring the manufacture of wood-based products with regard to the emission of volatile organic compounds, and devices for monitoring the emission of volatile organic compounds in the manufacture of wood-based products

FIELD OF DISCLOSURE

The invention relates to a method for monitoring the manufacture of wood-based products, including at least one pressing process, with regard to the emission of volatile organic compounds from the wood-based products, in which the concentration of the volatile organic compounds is recorded during production.

The invention also relates to devices for monitoring the manufacture of wood-based products with regard to the emission of volatile organic compounds from the wood-based products, in particular for carrying out the aforementioned method.

BACKGROUND OF THE INVENTION

Wood-based products are subject to certain limit values with regard to the release of volatile organic compounds, in particular with regard to their formaldehyde release, the level of which varies depending on the sales region or the customer. In recent years, there have been repeated reductions in these limit values, a trend that is expected to continue in the future.

Compliance with the legal requirements is ensured by using so-called reference test methods, which also differ from region to region. In Europe, for example, the chamber methods according to EN 717-1 and DIN EN 16516 are used as reference methods, while in North America the reference methods are ASTM E 1333 and ASTM D 6007. The determination of the formaldehyde release in the chamber extends over a period of up to 28 days (European method) or includes conditioning for several days and a test lasting around one day (North American methods). These tests are carried out for control purposes in the laboratories of testing institutes and serve as the basis for certifying the testing activities of wood-based material manufacturers. For everyday use, reference test methods are unsuitable for direct production monitoring and production control due to the sometimes very long test times (up to 28 days). Fast test methods are therefore used for factory production control, the results of which are later correlated with the results of the reference test methods. Here, too, there are regional differences: In Europe, example, for the gas analysis method (described in DIN EN ISO 12460-3) and the perforator method (DIN EN ISO 12460-5) are mainly used. In the Pacific region, desiccator tests according to JIS A 1460 or JAS in Japan and in the Pacific region, perforator and DMC (Dynamic Microchamber) in North America.

DE 10 2019 114 035 A1 describes a device in which sample gas is taken from various points (usually at extraction points) in the process via a gas probe and the amount of formaldehyde released is analysed there using FTIR, NIR, IMS and other methods. The results obtained are then correlated directly with the laboratory test values.

A method is also known from DE 10 2007 061 666 84 in which chip material from the sawing cut of the board strand is used to measure the formaldehyde released from the chips using suitable gas sensors (FTIR) or wet-chemical methods (photometry) and thus derive criteria for process control.

US 2009/0 230 306 A1 describes a method for predicting the formaldehyde emission from spectroscopic information measured directly on the material board using NIR spectroscopy.

DE 699 37 675 T2 discloses a method for controlling a wood-based material production process with regard to various product properties, including emissions. Here, multivariate analysis (for example least squares method-PLS) is used to predict the influence of a material addition (e.g. glue/hardener ratio) on the product property. The product properties are also analysed in-line, at-line or online using NIR spectroscopy, inter alia.

The method currently used day-to-day is the determination of formaldehyde release in the factory laboratories of the wood-based materials industry. Samples cut from the manufactured boards are used here. There are several hours between production and receipt of the test results, due to the fact that the boards must first be cooled from around 100° C. to room temperature and sanded after production; in addition, the determination of the formaldehyde release itself takes several hours (depending on the method).

Wood-based material production is generally a continuous production process, but as emission test results are only available after a long delay, they cannot be used immediately for process optimisation. If a limit value is later found to have been exceeded in the laboratory, this often results in the production of rejects and the associated costs. As testing capacities are also severely limited by the number of test systems and personnel, the majority of production remains untested. In the worst-case scenario, an exceeded limit value is not noticed in the factory and only becomes apparent during inspections by the authorities. This then results in very costly recall campaigns and correspondingly negative marketing.

SUMMARY OF THE INVENTION

To prevent these problems, continuous production monitoring is necessary. However, existing continuous measurement methods are time-consuming or provide inaccurate predicted values that do not allow reliable prediction of formaldehyde release in the laboratory and the end product. Reliable process control with regard to the later formaldehyde emission of the wood-based material produced can therefore hardly be achieved with the established methods. This requires the consideration of a number of process parameters that have an influence on the measurement result. Measurement in extraction devices is particularly challenging in this respect, as not only formula parameters (such as board feed rate, board thickness, board weight, press temperature, etc.) can have an influence, but also indirect factors such as the volume flow of the extraction and the material moisture before the pressing process. In addition, the installation and measurement conditions major challenges for the measurement technology used. The following areas of application can be distinguished here:

a.) material-carrying extraction: These extraction systems remove the material that falls off during the sawing cut (e.g. through diagonal sawing or edge trimming) of the board strand in the process. These installation locations have proven to be particularly suitable for in-situ measurements in terms of the significance of the results. However, the material transported in the air can interfere with the measurement due to adhesion/deposition. Particularly with optical measurements such as TDLS (Tunable Diode Laser Spectroscopy), the laser beam path can be interrupted by deposits. Accordingly, a special device is required to keep the laser optics clean.

b.) Non-material-carrying extraction: These systems can be located above the star turner, for example, or along the roller conveyor. In general, a measurement can also be carried out here, but in terms of the quality of the later correlations, they tend to be inferior to the material-carrying extraction.

c.) "Open path" application: Another option is to measure the board emission using TDLS directly in the gas phase above the material. In principle, any point in the process where the material is transported over a roller conveyor is suitable here. An example of this is the outlet of the star turner. However, this measuring arrangement is strongly influenced by environmental influences (in particular convection in the hall), which is why a special device is also required here to protect the beam path from environmental influences.

Methods of the aforementioned type are known from WO 2013/109 853 A1, DE 20 2019 102 959 U1 and DE 10 2011 017 280 A1.

The object of the invention is thus that of disclosing a method of the type mentioned at the outset, with which continuous measurement and determination of the emission of volatile organic compounds from wood-based products is made possible. Furthermore, corresponding monitoring devices of the kind likewise mentioned at the outset are to be disclosed, with which the method can be carried out.

With regard to the method, the problem is solved in accordance with the invention in that the concentration of the volatile organic compounds is detected during an extraction of product parts or of a product surface using the TDLS (Tunable Diode Laser Spectroscopy) measurement method, in that the detected concentration of the volatile organic compounds is fed to a mathematical model and in that parameters such as product thickness, areal density, feed rate of the product strand, flow rate in an extraction of product parts or of the product surface and the moisture content of the raw materials for the wood-based products are determined before the pressing process and are also fed to the mathematical model.

The process-related solution therefore includes a measurement method for determining the emission of volatile organic compounds from a wood-based product during the production process. A wood-based product is defined here as any type of wood-based product that is produced with glues containing formaldehyde. The calculated value of the formaldehyde emission here refers to the laboratory test value determined using the gas analysis method (DIN EN ISO 12460-3) or to another laboratory test value as part of the factory's own quality control. In principle, however, the model can also be used to predict the results of other emission test methods.

For the measurement method, the formaldehyde concentration in the process is recorded and fed together with other formula and process parameters to a mathematical model, which then predicted calculates a value for the formaldehyde emission of the board. For this purpose, the mathematical model performs a multivariate data analysis, typically using the PLS method (least squares method). The PLS method has proven to be particularly reliable for analysing the emission data, but other methods of multivariate analysis (such as multiple linear regression, MLR) can also be used for the analysis. In principle, any possible position downstream of a press for the products can be considered as a measuring point for the formaldehyde concentration. The chip extraction systems of diagonal and trimming saws are particularly suitable for this. Parallel to the formaldehyde concentration, several parameters related to the formaldehyde emission and concentration must be recorded from the process and the formula. The data is synchronised and transferred to the mathematical model. The mathematical model is determined in two steps. In the first step, all available parameters and the formaldehyde emission value from the gas analysis are used to model the prediction algorithm for calculating the formaldehyde emission value, for example. In the second step, predicted values for the formaldehyde emission are calculated using the and formula only process parameters the and formaldehyde concentrations measured in the process. The predicted value is calculated here without any time delay, thus enabling continuous monitoring of production.

The method according to the invention thus enables an immediate determination of the emission of volatile organic compounds.

According to a development of the method according to the invention, further parameters from the manufacture of the wood-based products can be transferred to the mathematical model, which advantageously increases the accuracy of the prediction of the emission. These parameters can be:

- the temperature of existing heating circuits of the pressing device
- the degree of gluing of existing product layers the molar ratio of the glue used in the product layers
- the proportion of surface layers in relation to the total product
- the share of the middle layer in relation to the total product, and
- the amount of urea added to the product layers.

Further process data can improve the accuracy of the prediction, but investigations have shown that the prediction model is sufficiently accurate with the parameters mentioned here (approximately ±5%). This method makes it possible to determine and monitor the later formaldehyde emission of the product during production. This makes it possible for the first time to intervene directly in the production process if the product requirements with regard to formaldehyde emissions are not likely to be met.

According to a further development of the invention, it is provided that the concentration value measured from the product parts or the emission from the product surface and corrected by the mathematical model is referenced against the gas analysis method (DIN EN ISO 12460-3) or any other standardised laboratory test method. This reference makes it possible to check the predicted values in the laboratory and to continually optimise the algorithm. Furthermore, the system can be recalibrated with little effort in the event of major changes to the production process or the equipment. If the predicted value is sufficiently accurate and reliable, it is also conceivable in the best case to completely replace the laboratory test with the process measurement. With sufficient data from test values, the method according to the invention also makes it possible to predict the effects of component additions on the emissions. This makes it possible to control the manufacturing process of the wood-based products.

If a suitable measurement method is selected, the method according to the invention can be carried out in situ.

A first solution to the problem on the device side is characterised in that the device has transmitter unit and receiver unit components arranged on both sides of an extraction line carrying product parts, in that these components are connected to the extraction line via pipe sections, and in that at least one flushing device is associated with the pipe sections.

The transmitter unit and receiver unit are arranged opposite each other in relation to an extraction line carrying product parts, so that signals emitted by the transmitter unit are guided through the extraction line and then picked up by the receiver unit. The transmitter unit and the receiver unit are connected here to the extraction line via pipe sections, with the result that product parts guided in the extraction line can penetrate these pipe sections and may also clog these pipe sections. Therefore, according to the invention, the pipe sections are associated with the flushing device, which causes the pipe sections to be flushed alternately. Free measurement of the product through the extraction line is thus advantageously restored.

The flushing device preferably has flushing pipes that can be pressurised with compressed air. The pressurisation of the compressed air can preferably be alternating with regard to the direction of the compressed air introduced. Alternating pressure surges, e.g. at 10-minute intervals, reliably remove deposits from product parts. The flushing pipes are preferably inserted into the pipe sections for connecting the transmitter unit and receiver unit to the extraction line. The transmitter unit therefore transmits through the flushing pipes to the receiver unit, and flushing with compressed air keeps the measuring path clear.

For the further design of this device, it is also provided that each flushing pipe has a free end with a conical design that protrudes into the extraction line. The conical, tapered ends of the flushing pipes prevent product parts from entering the flushing pipe and thus the pipe section.

In another embodiment of the solution to the problem on the device side, it is provided that the device has at least one protective housing for receiving the wood-based products, that components arranged on both sides of the protective housing are the transmitter unit and the receiver unit, and that at least one air guiding device is associated with the protective housing.

With this device, measurement is possible directly above the wood-based products. These are guided through the housing provided, and the transmitter unit and the receiver unit are again assigned to the housing on both sides. The housing is equipped with at least one air conveying device that triggers air movement in the housing.

It is envisaged here that the transmitter unit and receiver unit are arranged in a plane above the wood-based products. The air conveying devices can still be arranged above the transmitter unit and receiver unit and can comprise at least one fan inserted into the housing wall.

For both devices, a laser source for the TDLS (Tunable Diode Laser Spectroscopy) measurement method can be used as the transmitter unit.

BRIEF DESCRIPTION OF THE DRAWINGS

Exemplary embodiments of the device according to the invention are shown in the drawing, in which.

DETAILED DESCRIPTION

Figure 1:
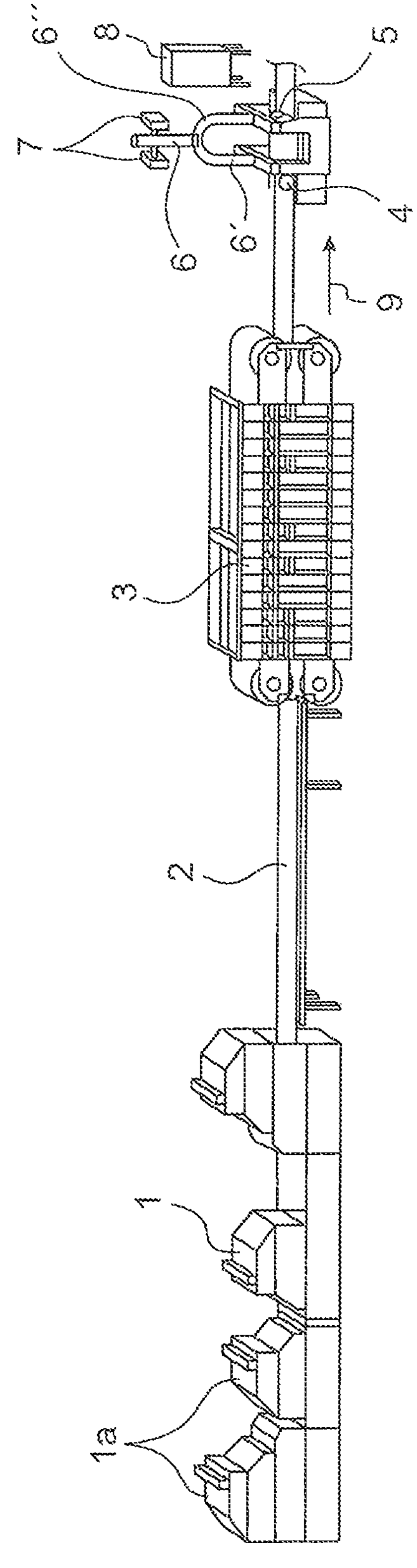
FIG. 1: shows a schematic side view of a continuous-strand production line for wood-based products, to which a device according to the invention is assigned for surface monitoring.

Manufacture of the continuous strand 2 begins in a forming line 1 with spreaders 1*a*. The continuous strand 2 emerges from the forming line 1 in the form of a chip cake and is fed to a press system 3 using suitable conveyors. After leaving this press system 3, the continuous strand 2 is in compressed form. It is fed along arrow 9 to a trimming saw 4 and a diagonal saw 5.

Figure 2:
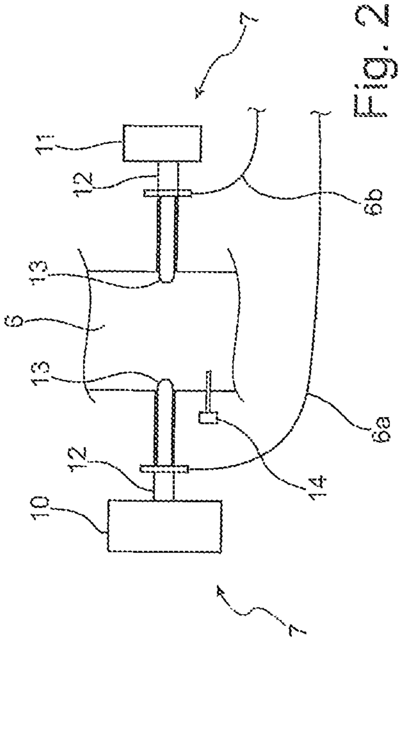
FIG. 2: shows a schematic side view of the monitoring device according to the invention according to FIG. 1.

The monitoring device according to the invention is assigned to the saws 4 and 5. Specifically, it is assigned to an extraction system 6 of the saws 4 and 5. Each saw 4 and 5 initially has its own extraction channel 6, 6", which then open out into the common extraction line 6, designed as a pipe. The monitoring device according to the invention has components 7, which are arranged on both sides of the extraction line 6 (FIG. 2). The components 7 are connected to a control cabinet 8 for their control.

FIG. 2 shows the extraction line 6 in portions. The components 7 are arranged on both sides of this extraction line 6; these components 7 are a transmitter unit 10 and a receiver unit 11.

The transmitter unit 10 and the receiver unit 11 are connected to the extraction line 6 via pipe sections 12. Each pipe section 12 runs from the transmitter unit 10 or from the receiver unit 11 to the surface of the extraction line 6, wherein an opening is arranged in the wall of the extraction line 6 in the attachment region of the pipe section 12 at the surface. The transmitter unit 10 and receiver unit 11 are thus connected to the inside of the extraction line 6.

Flushing pipes 13 are inserted into the pipe sections 12. The flushing pipes 13 have a slightly smaller diameter than the pipe sections 12 so that the flushing pipes 13 can be arranged inside the pipe sections 12. The free ends of the flushing pipes 13 protrude into the interior of the extraction line 6, and their free ends are conical.

A volume flow sensor 14 is also assigned to the extraction line 6. Said sensor is attached, below the pipe section 12 for the transmitter unit 10, to the extraction line 6, protruding into the interior of the extraction line 6.

Figure 3:
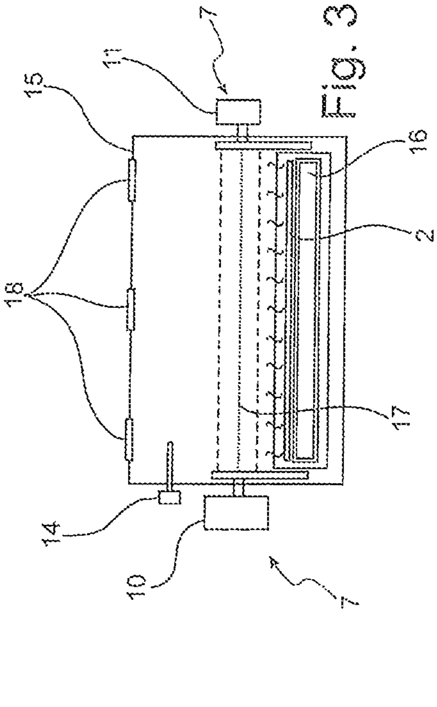
FIG. 3: shows an alternative design of a monitoring device for monitoring the continuous-strand production line in FIG. 1.

In the exemplary embodiment according to FIG. 3, no extraction line 6 is provided for the monitoring device. A protective housing 15 is used here, through which the continuous strand 2 is guided. A transmitter unit 10 and a receiver unit 11 are again arranged on the outside of the protective housing 15. The arrangement is provided at a height above the continuous strand 2, which rests on a substrate 16. For example, a laser source is used as the transmitter unit 10 and the laser beam emitted by the transmitter unit 10 is illustrated by the dashed line 17. It runs through the inside of the protective housing 15 to the receiver unit 11.

Another volume flow sensor 14 is arranged in the protective housing 15. It is arranged above the plane of the transmitter unit 10 and receiver unit 11 on a wall of the protective housing (15). Fans 18 are also arranged above this plane, in the ceiling of the protective housing 15.

The invention claimed is:

1. A method for monitoring a manufacture of wood-based products, including at least one pressing process, with regard to an emission of volatile organic compounds from the wood-based products, in which a concentration of the volatile organic compounds is detected during manufacture, the method comprising:

measuring, in situ, the concentration of volatile organic compounds during an extraction of product parts or of a product surface using TDLS (Tunable Diode Laser Spectroscopy), FTIR, NIR, IMS or photoacoustics;

feeding a detected concentration of volatile organic compounds into a mathematical model;

determining parameters, including product thickness, areal density, production feed rate, flow rate in the extraction of the product parts or of the product surface and a moisture content of the raw materials for the wood-based products, before the at least one pressing process; and feeding the parameters into the mathematical model.

2. The method according to claim 1, further comprising feeding a parameter of temperature of existing heating circuits of a pressing device into the mathematical model.

3. The method according to claim 1, further comprising feeding a parameter of a degree of gluing of existing product layers into the mathematical model.

4. The method according to claim 3, further comprising feeding a molar ratio of a glue used in the existing product layers into the mathematical model.

5. The method according to claim 3, further comprising feeding a proportion of cover layers or of middle layers, of the existing product layers, in relation to a total product into the mathematical model.

6. The method according to claim 3, further comprising feeding an amount of urea added to the existing product layers into the mathematical model.

7. The method according to claim 1, wherein an emission of the product parts is corrected by the mathematical model or an emission from the product surface is compared to a standardized laboratory emission test method.

8. The method according to claim 7, further comprising:

correcting a concentration of the volatile organic compounds by the mathematical model; and using a corrected concentration of the volatile organic compounds for open-loop and closed-loop control of the manufacture of wood-based products, including the at least one pressing process.

9. A device for monitoring the manufacture of wood-based products with respect to the emission of volatile organic compounds from the wood-based products, for carrying out the method according to claim 1, the device comprising:

a transmitting unit and a receiving unit, arranged on opposite sides of an extraction line carrying product parts and connected to the extraction line via pipe sections; and at least one flushing device connected to the pipe sections.

10. The device according to claim 9, wherein the transmitter unit comprises at least one laser source for the TDLS (Tunable Diode Laser Spectroscopy) measurement method.

11. The device according to claim 9, wherein the flushing device has flushing pipes which can be supplied with compressed air.

12. The device according to claim 11, wherein with a pressurization of the compressed air is alternating.

13. The device according to claim 11, wherein the flushing pipes are inserted into the pipe sections for connecting the transmitter unit and receiver unit to the extraction line.

14. The device according to claim 11, wherein each of the flushing pipes has a free end with a conical design that protrudes into the extraction line.

15. A device for monitoring the manufacture of wood-based products with regard to the emission of volatile organic compounds from the wood-based products, for carrying out the method according to claim 1, the device comprising:

at least one protective housing for receiving the wood-based products;

a transmitter unit and a receiver unit arranged on opposite sides of the protective housing; and at least one air guiding device connected to the protective housing.

16. The device according to claim 15, wherein the transmitter unit and the receiver unit are arranged in a plane above the wood-based products.

17. The device according to claim 15, wherein the at least one air guiding device includes at least one fan inserted into a wall of the protective housing.

18. The device according to claim 17, wherein the at least one fan is arranged above the transmitter unit and receiver unit.

19. The device according to claim 17, wherein the transmitter unit comprises at least one laser source for the TDLS (Tunable Diode Laser Spectroscopy) measurement method.

* * * * *